United States Patent [19]

Nelson

[11] 4,437,471
[45] Mar. 20, 1984

[54] IMPLEMENT FOR MEASURING SKIN TEMPERATURES

[76] Inventor: Jeffrey Nelson, 20 Allison Rd., Newport News, Va. 23602

[21] Appl. No.: 339,061

[22] Filed: Jan. 13, 1982

[51] Int. Cl.³ .................... A61B 10/00; G01N 11/12
[52] U.S. Cl. .................................. 128/736; 128/742; 374/162
[58] Field of Search ................ 374/162, 161; 128/736; 116/207, 216

[56] References Cited

U.S. PATENT DOCUMENTS

| | | | |
|---|---|---|---|
| 3,059,474 | 10/1962 | Keller et al. | 116/207 X |
| 3,568,627 | 3/1971 | Selinger | 116/207 |
| 3,620,889 | 11/1971 | Baltzer | 374/162 X |
| 3,951,133 | 4/1976 | Reese | 128/736 |
| 3,983,753 | 10/1976 | Greenleaf et al. | 374/208 |
| 4,019,368 | 4/1977 | Navato | 116/207 X |
| 4,060,654 | 11/1977 | Quenneville | 128/736 X |
| 4,064,872 | 12/1977 | Caplan | 374/162 |
| 4,070,912 | 1/1978 | McNaughtan | 374/162 |
| 4,208,910 | 6/1980 | Lezins | 374/109 |

*Primary Examiner*—Daniel M. Yasich
*Attorney, Agent, or Firm*—Mitchell B. Wasson; Martin P. Hoffman

[57] ABSTRACT

An implement for measuring an individual's skin temperature which is convenient and easy to use. Two liquid crystal indicators are attached to a base which is convenient to the user. When the user touches the implement, the liquid crystals would indicate how close the individual is to an individually tailored goal temperature which is a function of the state of relaxation of the individual. Depending upon how close the individual is to his goal temperature, a number of learned relaxation "cues" is utilized to help the individual obtain his goal temperature.

5 Claims, 4 Drawing Figures

U.S. Patent     Mar. 20, 1984     4,437,471
FIG. 1.
FIG. 2.
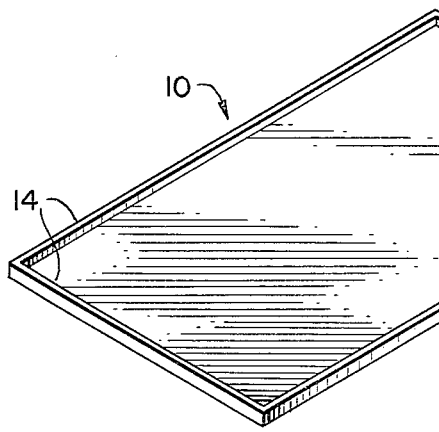
FIG. 3.
FIG. 4.
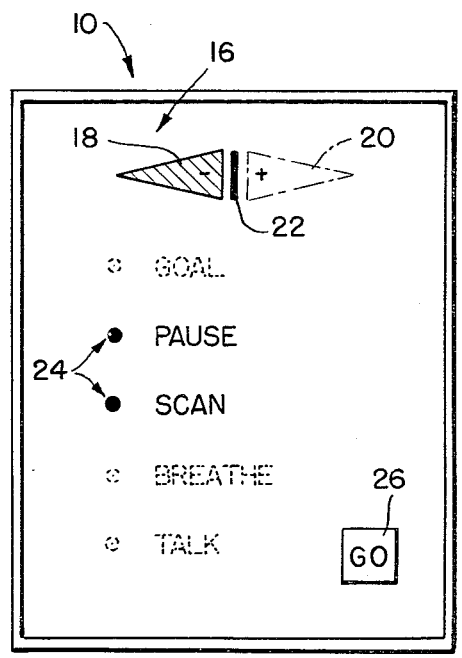
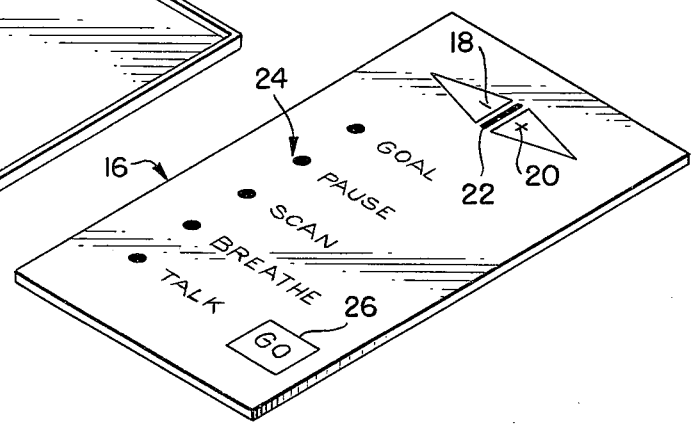
| ARROW AND COLOR | EXPLANATION |
|---|---|
| | 80-82° |
| | 82-85° |
| | 85-88° |
| | 88-89° |
| | 92° |
| | 92-93° |
| | 93-95° |
| | 95°+ |

IMPLEMENT FOR MEASURING SKIN TEMPERATURES

FIELD OF THE INVENTION

This invention relates generally to a device for measuring an individual's skin temperature thereby giving an indication of the individual's degree of relaxation or tenseness.

BACKGROUND OF THE INVENTION

Doctors, researchers and physiologists have, for many years, monitored a plurality of physiological variables such as heart rate, respiration rate and skin temperature to determine whether an individual has any effective control over the variables. These researchers have discovered that the individual does have a control over these variables and that this control is very important both to the psychological as well as the physiological well being of the individual. They have learned that when the individual is relaxed, these physiological variables are different than when the person is excited or under stress. Therefore, teaching the individual to consciously moderate these variables would allow the individual to become more relaxed. The relaxation reduces such stress-created ailments such as headaches, tension and high blood pressure.

For example, researchers have determined that the temperature of an extremity, such as a fingertip, is proportional to the rate of blood flow through the extremity. The autonomic nervous system controls the rate of blood flow to all parts of the body, including these extremities. Sympathetic stimulation reduces the blood flow to the extremities. Thus, fingertip temperature varies inversely with the activity of the sympathetic branch of the autonomic nervous system. Monitoring fingertip temperature and rendering it in visible or audible form reveals the state of activity of the sympathetic nervous system, as well as the related state of skeletomuscular and smooth muscular relaxation. In simple terms, the higher the individual's temperature, the more relaxed that person is. Conversely, a low skin temperature would indicate that the person is tense and under stress.

Typically, the individual is connected via a number of electrodes to a visual monitor such as an oscilliscope which would directly indicate to the individual his or her skin temperature. If the individual exhibits a low skin temperature, the researcher or physiologist would try various techniques for endeavoring the individual to relax. If these techniques succeed, the individual's skin temperature would increase, a condition which would become visually apparent to the individual via the oscilliscope. Since the individual learns that a particular technique of relaxation is effective, presumably the individual could re-utilize this technique when it became apparent that he was under stress. While this technique has proven efficacious when the individual has been made aware that his skin temperature has indicated a degree of tenseness, this technique is shown to be inadequate under normal circumstances when the individual is not directly connected to the visual monitor, such as the oscilliscope.

Accordingly, it is an object of the present invention to provide a new and improved technique and device for monitoring the skin temperature of the individual without the necessity of positively connecting the individual to a visual response monitor.

An additional object of the present invention is to provide a device for measuring the skin temperature which is relatively unobtrusive, therefor allowing the individual to utilize the device in situations such as sales meetings or under presentations in which the individual is likely to be under stress.

U.S. Pat. No. 1,575,262 issued to Leopold Greiner, Jr. is directed to a skin thermometer which includes a bulb of glass tubing wound into a spiral form connected to a standard thermometer. The tubing is placed against the skin and the temperature thereof is indicated on the thermometer. Due to its construction, this patent would have little use in the type of situation described above.

Furthermore, U.S. Pat. No. 3,983,753 issued to John E. Greenleaf and Bill A. Williams describes a thermometer holder for skin temperature measurements. However, similar to the patent to Greiner, Jr., a thermometer used in conjunction with this holder would be difficult to use in the various situations in which the present invention is contemplated.

U.S. Pat. No. 3,951,133 issued to John Reese describes a device which is placed around an individual's finger for displaying skin temperature changes. The device includes two or more sheets of liquid crystal thermofilm which are responsive to the skin temperature. Each sheet is responsive to different temperature ranges and therefor depending upon the color of each of the sheets, the skin temperature of the individual can be visualized. However, due to the fact that each sheet is responsive to only a range of temperatures, the exact temperature of the skin cannot be determined.

Applicant is the inventor of co-pending U.S. Application Ser. No. 245,527 filed on March 19, 1981, now abandoned relating to providing an accurate indication of an individual's skin temperature which includes a liquid crystal temperature sensing means provided on an elongated cylindrical member such as a pen or pencil. The body of the pen or pencil is metallic to create a heat sink thereby insuring that the skin temperature is accurately relayed to the temperature monitoring and indicating means. While the co-pending application does accurately measure the individual's skin temperature, this measurement has meaning only when compared to a goal temperature for the particular individual. Furthermore, an indication that the individual's temperature is either too low or too high with respect to the goal is not helpful unless the individual can then determine what must be done to diminish the difference between the individual's actual temperature and that of the individual's goal temperature.

Consequently, it is another object of the present invention to provide a device which not only indicates the actual skin temperature of an individual, but would also indicate what the individual should do to allow the individual to reach his or her goal temperature.

SUMMARY OF THE INVENTION

The present invention relates to a device which can be easily and unobtrusively manipulated by an individual so as to measure the individual's skin temperature, thereby giving a visual indication of the state of relaxation of the individual. The device contains a planar backing member into which a strip containing a plurality of liquid crystal displays can be inserted. Two of these displays are utilized to indicate whether the individual's skin temperature corresponds to his or her goal temperature, or to illustrate how much the individual's actual temperature is above or below the goal temperature. Additionally, depending upon the actual skin temperature, a plurality of liquid crystal "cues" is utilized to assist the individual in obtaining his or her goal temperature.

The above other objects and features of the invention will become apparent from the following detailed description taken in conjunction with the accompanying drawings and claims to form a part of this specification.

BRIEF DESCRIPTION OF THE DRAWING

FIG. 1 is a top view of the temperature measuring device without the liquid crystal strip insert;

FIG. 2 is a top view of the temperature measuring device with the inclusion of the liquid crystal strip insert;

FIG. 3 is a top view of the temperature measuring device as shown in use; and

FIG. 4 is a chart depicting various temperature ranges of several of the liquid crystal indicators.

DETAILED DESCRIPTION OF THE DRAWING

As shown in FIG. 1, the temperature measuring device 10 consists of a square or rectangular base member 12 into which a strip 16 containing a plurality of compartmentalized liquid crystals is to be inserted. The base member 12 contains a frame 14 which extends around said member and is slightly reset therefrom to allow the insertion of the liquid crystal strip 16. Although the exact dimensions of the device are not important, the typical temperature measuring device can be approximately two to four inches on each side.

The liquid crystal strip insert 16, as shown in FIG. 2, contains two liquid crystal compartments 18 and 20 which indicate whether the individual's skin temperature is above or below that of his or her goal temperature which is indicated at 22. Liquid crystal compartment 18 includes a minus sign therein, indicating that when the compartment becomes visible, the individual's skin temperature is below that of the goal temperature. The minus sign could also be permanently affixed to strip 16 or located in proximity to compartment 18. Liquid crystal compartment 20 includes a positive sign in a manner similar to the minus sign associated with compartment 18. Therefore, when compartment 20 becomes visible, the individual's skin temperature exceeds the goal temperature. This goal temperature could be indicated by a permanent marking on the strip 16 or also could be provided by a liquid crystal material. As is shown in the art, liquid crystal devices remain relatively clear for a wide temperature range and then would become a certain color only during a relatively narrow temperature range. Additionally, the state of the art of liquid crystal displays is such that a given liquid crystal compartment can change to various colors depending upon the particular temperature to which it has been subjected. The strip 16 can be constructed of a flexible metallic material, or any relatively flexible material which conducts temperature fairly rapidly.

As shown in FIG. 2, one liquid crystal compartment 18 is placed to the left of the goal temperature indication and a second liquid crystal compartment 20 is placed to the right of the goal destination. Liquid crystal compartment 18 is utilized to indicate that the individual's temperature is below the goal temperature and liquid crystal compartment 20 indicates that the temperature is above that of the goal. Typical operating values and colors of these liquid crystal compartments are shown in the chart of FIG. 4. It should be noted that the exact temperature ranges and the colors utilized to depict these ranges are not crucial, but they can change with respect to various parameters. Additionally, only one of the liquid crystal compartments 18 and 20 would be activated at any one time.

As shown in FIG. 4, a goal temperature of 90°-91° F. has been utilized. If the individual's skin temperature is much below that of the goal temperature, the liquid crystal compartment to the left of the goal indication 22 would become red. As the individual's skin temperature increases, but remains below that of the goal temperature, liquid crystal compartment 18 would change from red to yellow to green and then to blue. Once the individual's temperature exceeds that of the goal, the left liquid crystal compartment 18 would become colorless and the formerly colorless right liquid crystal compartment 20 would become red. As the individual's temperature increases, liquid crystal compartment 20 would change from red to yellow to green and then to blue. Since the liquid crystal strip 16 is removable from the preferably metal base 12, the temperature range of each liquid crystal compartment 18 and 20 could be adjusted during manufacture for person's whose goal temperatures might be lower or higher than that of 90°-91° F.

While the particularly colored liquid crystal compartments 18 and 20 can be interpreted by the individual in such a manner to indicate to that individual what must be done to reach the goal temperature, the present device also includes various "cues" 24 which would have meaning to the individual. These cues are contained in a liquid crystal compartment and would only be activated during particular temperature situations. Although the exact cues utilized can be varied, four cues are shown in FIG. 2 which would help the individual to reach his or her goal temperature. These cues are PAUSE, SCAN, BREATHE and TALK. Through the use of various seminars or literature, the individual realizes that the cue PAUSE indicates that he must relax in order for him to achieve the goal temperature. SCAN indicates that the individual should endeavor to relax his muscles. BREATHE indicates that the individual should concentrate to take long and deep breaths, and TALK would indicate to the indiviudal that various learned coping statements should be repeated.

If the actual skin temperature is relatively close to that of the goal temperature, only the PAUSE cue will be activated. As the skin temperature begins to deviate further from the goal temperature, the SCAN cue, the BREATHE cue and the TALK cue become progressively visable such that when the individual's temperature is considerably away from the goal temperature, all of the cues would be activated. As the individual comes closer and closer to his goal temperature, the cues will be deactivated one-by-one. As the goal temperature is achieved, the TALK cue would disappear followed by the BREATHE cue, the SCAN cue, and finally the PAUSE cue.

You will note that the cues are activated only when the minus liquid crystal compartment 18 is activated and not when the positive liquid crystal compartment 20 becomes visible. This occurs because the negative temperature indicates that the individual is under stress and the cues will help relieve the tension. When the goal temperature is exceeded, the individual is in a relatively relaxed state and the cues are not necessary.

Because the temperature indicating device can be subject to the temperature of its environment, the liquid crystal indicators used therewith have been found to achieve their best result with a room temperature of between 70°–82° F. Use of this device outside this temperature range may prove to be inaccurate. Therefore, the device includes an indicator 26 which would be activated only in an ambient temperature range between 70°–82° F. This liquid crystal compartment is depicted by the word GO and when this word is shown, the user knows that the device would accurately measure his skin temperature. Additionally, the liquid crystal cues 24 and the indicators 18 and 20 could be constructed such that, regardless of whether the individual touches the device, no indication would be made if the room temperature is either too hot or too cold. In this embodiment, liquid crystal compartment 26 would not be necessary.

In order to facilitate its use, the temperature measuring device described herein can be attached to various pieces of furniture such as desk sets or other things such as notebooks, credit cards or a wrist watch band which would then be easily utilized by the individual.

FIG. 3 shows the implement described herein in use. When the individual wishes to utilize the device, he merely places a finger anywhere on the surface of the strip 16. Since the material used to construct the strip is a good conductor of heat, the response to skin temperature is fairly rapid. Snce the minus compartment 18 is green, the skin temperature is between 85°–88° F. indicating a moderate degree of tenseness. Additionally, the PAUSE and SCAN cues are also activated. The individual utilizes these learned cues to relax. When his temperature is between 88°–89° F., the compartment 18 becomes blue and the SCAN cue becomes invisible. When the skin temperature reaches 90°–91° F., all of the cues and the compartments are invisible.

While preferred embodiments of the present invention have been shown and described herein, it will become obvious that numerous omissions, changes and additions may be made in these embodiments without departing from the spirit and scope of the present invention.

What is claimed is:

1. A device for indicating the state of relaxation or tension of an individual with respect to a particular optimum predetermined temperature of the individual as measured by the individual's fingertip skin temperature comprising:

a thermally conductive planar surface;

two temperature sensitive liquid crystal indicators located on said planar surface, one indicator only becoming visible when the individual's fingertip skin temperature is less than the predetermined temperature, and the second indicator only becoming visible when the individual's skin temperature is greater than the predetermined temperature; and a plurality of temperature sensitive liquid crystal relaxation cues located on said planar surface, said relaxation cues becoming visible only when the skin temperature of the individual is less than that of the predetermined temperature of the individual, wherein said temperature sensitive liquid crystal indicators indicate the proximity of the individual's fingertip skin temperature to that of the predetermined temperature and said temperature sensitive relaxation cues assist the individual in attaining the predetermined temperature by allowing the individual to recall certain learned relaxation techniques.

2. A device for indicating the state of relaxation or tension of an individual in accordance with claim 1, wherein the temperature range of each of said temperature sensitive relaxation cues overlaps but is different than the temperature range of the remaining temperature sensitive relaxation cues, such that as the skin temperature of the individual approaches the predetermined temperature, the number of temperature sensitive relaxation cues visible to the individual decreases.

3. A device for indicating the state of relaxation or tension of an individual in accordance with claim 1 wherein said temperature sensitive liquid crystals change colors depending upon the skin temperature of the individual.

4. A device for indicating the state of relaxation or tension of an individual in accordance with claim 1, further including a means provided on said planar surface sensitive to the ambient temperature of the surroundings.

5. A device for indicating the state of relaxation or tension of an individual in accordance with claim 1 further including a planar base member having a recessed frame around at least a portion of its periphery for insertion of said planar surface therein.

* * * * *